United States Patent
Gagnieux et al.

(10) Patent No.: US 6,679,864 B2
(45) Date of Patent: Jan. 20, 2004

(54) SAFETY SHIELD SYSTEM FOR PREFILLED SYRINGES

(75) Inventors: Samuel Gagnieux, Grenoble (FR); Hubert Jansen, Marburg-Michelbach (DE)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/876,710

(22) Filed: Jun. 7, 2001

(65) Prior Publication Data

US 2003/0050607 A1 Mar. 13, 2003

Related U.S. Application Data

(63) Continuation-in-part of application No. 09/838,032, filed on Apr. 19, 2001, which is a continuation-in-part of application No. 09/290,786, filed on Apr. 12, 1999, now Pat. No. 6,319,233.
(60) Provisional application No. 60/082,221, filed on Apr. 17, 1998.

(51) Int. Cl.$^7$ .................................................. A61M 5/32
(52) U.S. Cl. ..................................... 604/198; 604/110
(58) Field of Search ................................ 604/110, 181, 604/192, 198, 187

(56) References Cited

U.S. PATENT DOCUMENTS

| | | | |
|---|---|---|---|
| 2,023,289 A | 12/1935 | Pringle | |
| 2,801,741 A | 8/1957 | Harkness et al. | |
| 2,851,157 A | 9/1958 | Christman | |
| 2,876,770 A | 3/1959 | White | 128/215 |
| 3,076,455 A | 2/1963 | McConnaughey et al. | |
| 4,068,661 A | 1/1978 | Hennings | 128/215 |
| 4,285,105 A | 8/1981 | Kirkpatrick | |
| 4,361,149 A | 11/1982 | Worder | 128/215 |
| 4,425,120 A | 1/1984 | Sampson et al. | 604/198 |
| 4,573,976 A | 3/1986 | Sampson et al. | 604/198 |
| 4,585,445 A | 4/1986 | Hadtke | |
| 4,598,820 A | 7/1986 | Murphy | 206/328 |
| 4,631,057 A | 12/1986 | Mitchell | |
| 4,695,274 A | 9/1987 | Fox | 604/198 |
| 4,723,943 A | 2/1988 | Spencer | |
| 4,723,945 A | 2/1988 | Theiling | 604/232 |
| 4,737,144 A | 4/1988 | Choksi | |
| 4,743,233 A | 5/1988 | Schneider | |
| 4,747,837 A | 5/1988 | Hauck | |
| 4,758,231 A | 7/1988 | Haber et al. | |
| 4,801,295 A | 1/1989 | Spencer | |
| 4,804,372 A | 2/1989 | Laico et al. | 604/198 |

(List continued on next page.)

FOREIGN PATENT DOCUMENTS

| | | |
|---|---|---|
| AU | A-52050/96 | 11/1996 |
| DE | 38 23 266 C2 | 12/1998 |
| DE | 195 43 313 C2 | 7/1999 |
| EP | 0 467 173 A1 | 1/1994 |

(List continued on next page.)

*Primary Examiner*—Michael J. Hayes
*Assistant Examiner*—Lina R Kontos
(74) *Attorney, Agent, or Firm*—David M. Fortunato

(57) ABSTRACT

A medical injection device is provided which includes a shield system and a syringe which may be coupled to the shield system. The shield system includes a syringe holder, a shield telescopically received in the holder and slidably coupled to the holder and an end fitting which isolates the syringe flange from the holder, preventing damage to the flange. A spring resiliently urges the shield from a retracted position to an extended position. Stop members are provided adjacent the distal end of the holder and the proximal end of the shield for maintaining the shield in the retracted position. The syringe is slidably coupled to the holder, and extends within the shield. Axial movement of the syringe with respect to the holder causes disengagement of the stop members, allowing the spring to move the shield to the extended position. Detents are provided on the holder for maintaining the shield in the extended position.

22 Claims, 4 Drawing Sheets

U.S. PATENT DOCUMENTS

| Patent | Date | Name | Ref |
|---|---|---|---|
| 4,826,491 A | 5/1989 | Schramm | |
| 4,840,185 A | 6/1989 | Hernandez | |
| 4,850,994 A | 7/1989 | Zerbst et al. | 604/198 |
| 4,863,434 A | 9/1989 | Bayless | |
| 4,871,355 A | 10/1989 | Kikkawa | |
| 4,874,382 A | 10/1989 | Lindemann et al. | 604/195 |
| 4,892,521 A | 1/1990 | Laico et al. | 604/192 |
| 4,894,055 A | 1/1990 | Sudnak | 604/198 |
| 4,897,083 A | 1/1990 | Martell | 604/192 |
| 4,900,310 A | 2/1990 | Ogle, II | |
| 4,911,693 A | 3/1990 | Paris | 604/192 |
| 4,917,673 A | 4/1990 | Coplin | |
| 4,923,445 A | 5/1990 | Ryan | |
| 4,923,447 A | 5/1990 | Morgan | 604/198 |
| 4,927,018 A | 5/1990 | Yang et al. | |
| 4,927,416 A | 5/1990 | Tomkiel | 604/198 |
| 4,932,937 A | 6/1990 | Gustavsson et al. | |
| 4,947,863 A | 8/1990 | Haber et al. | |
| 4,985,021 A | 1/1991 | Straw et al. | |
| 4,994,045 A | 2/1991 | Ranford | |
| 4,998,920 A | 3/1991 | Johnson | |
| 4,998,924 A | 3/1991 | Ranford | 604/798 |
| 5,011,479 A | 4/1991 | Le et al. | 604/198 |
| 5,019,051 A | 5/1991 | Hake | 604/198 |
| 5,024,660 A | 6/1991 | McNaughton | |
| 5,045,066 A | 9/1991 | Scheuble et al. | |
| 5,053,018 A | 10/1991 | Talonn et al. | |
| 5,057,086 A | 10/1991 | Dillard, III et al. | |
| 5,057,087 A | 10/1991 | Harmon | |
| 5,059,185 A | 10/1991 | Ryan | |
| 5,066,277 A | 11/1991 | Carrell et al. | |
| 5,067,945 A | 11/1991 | Ryan et al. | |
| 5,078,698 A | 1/1992 | Stiehl et al. | |
| 5,084,030 A | 1/1992 | Byrne et al. | |
| 5,106,379 A | 4/1992 | Leap | |
| 5,108,378 A | 4/1992 | Firth et al. | |
| RE34,045 E | 8/1992 | McFarland | |
| 5,137,521 A | 8/1992 | Wilkins | |
| 5,141,500 A | 8/1992 | Hake | |
| 5,147,303 A | 9/1992 | Martin | |
| 5,163,918 A | 11/1992 | Righi et al. | |
| 5,169,392 A | 12/1992 | Ranford et al. | |
| 5,188,614 A | 2/1993 | Hart | |
| 5,197,953 A | 3/1993 | Colonna | 604/110 |
| 5,201,708 A | 4/1993 | Martin | 604/110 |
| 5,201,720 A | 4/1993 | Borgia et al. | |
| 5,217,437 A | 6/1993 | Talonn et al. | |
| 5,226,894 A | 7/1993 | Haber et al. | |
| 5,242,240 A | 9/1993 | Gorham | 403/391 |
| 5,242,420 A | 9/1993 | Martin | 604/198 |
| 5,256,154 A | 10/1993 | Liebert et al. | |
| 5,279,581 A | 1/1994 | Firth et al. | |
| 5,300,030 A | 4/1994 | Crossman et al. | 604/136 |
| 5,300,040 A | 4/1994 | Martin | 604/198 |
| 5,304,149 A | 4/1994 | Morigi | |
| 5,308,332 A | 5/1994 | Dillard, III et al. | |
| 5,312,365 A | 5/1994 | Firth et al. | |
| 5,318,538 A | 6/1994 | Martin | 604/110 |
| 5,318,547 A | 6/1994 | Altschuler | |
| 5,338,303 A | 8/1994 | King et al. | |
| 5,338,310 A | 8/1994 | Lewandowski | |
| 5,342,309 A | 8/1994 | Hausser | |
| 5,342,320 A | 8/1994 | Cameron | |
| 5,344,407 A | 9/1994 | Ryan | |
| 5,346,480 A | 9/1994 | Hess et al. | |
| 5,348,544 A | 9/1994 | Sweeney et al. | |
| 5,350,367 A | 9/1994 | Stiehl et al. | |
| 5,352,208 A | 10/1994 | Robinson | |
| 5,356,392 A | 10/1994 | Firth et al. | |
| 5,358,491 A | 10/1994 | Johnson et al. | |
| 5,368,578 A | 11/1994 | Covington et al. | |
| 5,380,296 A | 1/1995 | Smedley et al. | |
| 5,385,555 A | 1/1995 | Hausser | |
| 5,385,557 A | 1/1995 | Thompson | |
| 5,411,488 A | 5/1995 | Pagay et al. | |
| 5,411,489 A | 5/1995 | Pagay et al. | |
| 5,413,563 A | 5/1995 | Basile et al. | |
| 5,417,660 A | 5/1995 | Martin | 604/110 |
| 5,437,647 A | 8/1995 | Firth et al. | |
| 5,439,450 A | 8/1995 | Haedt | |
| 5,447,500 A | 9/1995 | Bergstresser et al. | |
| 5,458,577 A | 10/1995 | Kishigami | |
| 5,478,316 A | 12/1995 | Bitdinger et al. | 604/135 |
| 5,496,286 A | 3/1996 | Stiehl et al. | |
| 5,501,672 A | 3/1996 | Firth et al. | |
| 5,527,294 A | 6/1996 | Weatherford et al. | |
| 5,562,624 A | 10/1996 | Righi et al. | |
| 5,562,626 A | 10/1996 | Sampietro | |
| 5,601,535 A | 2/1997 | Byrne et al. | |
| 5,611,782 A | 3/1997 | Haedt | |
| 5,616,134 A | 4/1997 | Firth et al. | |
| 5,624,400 A | 4/1997 | Firth et al. | |
| 5,647,849 A | 7/1997 | Kalin | |
| 5,658,254 A | 8/1997 | Reicjenbach et al. | |
| 5,674,203 A | 10/1997 | Lewandowski | |
| 5,681,292 A | 10/1997 | Tober et al. | |
| 5,697,908 A | 12/1997 | Imbert et al. | 604/110 |
| 5,709,662 A | 1/1998 | Olive et al. | 604/135 |
| 5,713,871 A | 2/1998 | Stock | |
| 5,733,264 A | 3/1998 | Flowers | |
| 5,735,823 A | 4/1998 | Bergen | |
| 5,769,822 A | 6/1998 | McGary et al. | |
| 5,769,827 A | 6/1998 | DeMichele et al. | |
| 5,776,107 A | 7/1998 | Cherif-Cheikh | |
| 5,788,677 A | 8/1998 | Botich et al. | |
| 5,792,107 A | 8/1998 | Petrocelli | |
| 5,792,122 A | 8/1998 | Brimhall et al. | |
| 5,795,336 A | 8/1998 | Romano et al. | 604/192 |
| 5,797,885 A | 8/1998 | Rubin | |
| 5,800,395 A | 9/1998 | Botich et al. | |
| 5,800,403 A | 9/1998 | Pressly, Sr. et al. | |
| 5,800,404 A | 9/1998 | Poulsen | |
| 5,810,775 A | 9/1998 | Shaw | |
| 5,817,064 A | 10/1998 | DeMarco et al. | |
| 5,843,034 A | 12/1998 | Redfern et al. | |
| 5,843,036 A | 12/1998 | Olive et al. | 604/136 |
| 5,843,041 A | 12/1998 | Hake et al. | |
| 5,843,047 A | 12/1998 | Pyrozyk et al. | |
| 5,853,390 A | 12/1998 | Freschi | |
| 5,855,839 A * | 1/1999 | Brunel | 264/524 |
| 5,868,713 A | 2/1999 | Klippenstein | |
| 5,879,339 A | 3/1999 | Saito | |
| 5,882,342 A | 3/1999 | Cooper et al. | |
| 5,910,130 A | 6/1999 | Caizza et al. | 604/110 |
| 5,947,936 A | 9/1999 | Bonds | |
| 5,980,494 A | 11/1999 | Malenchek et al. | |
| 5,984,898 A | 11/1999 | Garvin | |
| 5,984,899 A | 11/1999 | D'Alessio et al. | 604/198 |
| 5,984,906 A | 11/1999 | Bonnichsen et al. | |
| 6,004,296 A | 12/1999 | Jansen et al. | 604/198 |
| 6,010,487 A | 1/2000 | DeMichele et al. | |
| 6,017,329 A | 1/2000 | Hake | 604/198 |
| 6,030,366 A | 2/2000 | Mitchell | |
| 6,033,387 A | 3/2000 | Brunel | 604/198 |
| 6,193,696 B1 | 2/2001 | Jansen et al. | 604/198 |
| 6,319,233 B1 | 11/2001 | Jansen et al. | 604/192 |

FOREIGN PATENT DOCUMENTS

| | | | |
|---|---|---|---|
| EP | | O 645 155 A2 | 3/1995 |

| | | |  | | | |
|---|---|---|---|---|---|---|
| EP | O 740 942 B1 | 11/1996 | | WO | WO 98/26824 | 6/1998 |
| EP | O 740 942 A1 | 11/1996 | | WO | WO 98/26825 | 6/1998 |
| EP | 0 845 275 A2 | 6/1998 | | WO | WO 98/35714 | 8/1998 |
| EP | O 864 335 A2 | 9/1998 | | WO | WO 99/16489 | 4/1999 |
| EP | 0740942 | 8/1999 | | WO | WO 99/22791 | 5/1999 |
| EP | 0 966 983 A1 | 12/1999 | | WO | WO 99/37343 | 7/1999 |
| EP | 0966983 | 12/1999 | | WO | WO 99/59658 | 11/1999 |
| EP | 1090652 | 4/2001 | | WO | WO 00/33900 | 6/2000 |
| WO | WO 92/19296 | 11/1992 | | WO | 0130427 | 5/2001 |
| WO | WO 97/02855 | 1/1997 | | | | |
| WO | WO 97/14455 | 4/1997 | | * cited by examiner | | |

SAFETY SHIELD SYSTEM FOR PREFILLED SYRINGES

CROSS REFERENCE TO RELATED APPLICATIONS

This application is a continuation-in-part application of Ser. No. 09/838,032 filed Apr. 19, 2001, which application is a continuation-in-part application of Ser. No. 09/290,786 filed Apr. 12, 1999, now U.S. Pat. No. 6,319,233, which application claims priority under 35 U.S.C. §119(e) to U.S. provisional patent application Ser. No. 60/082,221 filed Apr. 17, 1998.

BACKGROUND OF THE INVENTION

1. Field of the Invention

The field of the invention relates to shield systems for protecting against needle sticks, and syringes including such systems.

2. Brief Description of the Related Art

Syringes are well known medical devices for administering medicaments, drugs and vaccines to patients. Prefilled syringes are generally considered as those which are filled with a selected dosage of medicament, drug or vaccine by a pharmaceutical manufacturer for distribution to the end user. They are generally comprised of a glass barrel which contains the medicament, drug or vaccine, and a stopper slidably mounted within the barrel. The distal end of the barrel includes a needle cannula or the like affixed thereto or a connector for a needle cannula assembly such as a Luer fitting. The proximal end of the syringe includes an integral flange and is open to allow the insertion of a stopper of a plunger assembly. The plunger and stopper assembly allows the user to apply manual force to the plunger, causing the medicament, drug or vaccine to be delivered through the needle cannula or other piercing element. The healthcare worker or patient grips the flange and applies pressure to the plunger generally with the thumb.

The use of a sharp-pointed piercing element entails the risk of an accidental needle stick. To avoid such accidents, many prior art hypodermic syringes have included rigid cylindrical safety shields telescoped over the syringe barrel. These shields can be moved between a retracted position, where the needle is exposed for use, to an extended position where the needle is surrounded by the shield. U.S. Pat. Nos. 4,425,120, 4,573,976, 4,850,994 and 4,923,447 disclose various shield systems for hypodermic syringes. The latter two patents disclose shields which may be spring-actuated. It is ordinarily desirable to lock the needle shields in the protected positions, and a number of prior art designs provide for such locking. Some systems, such as those disclosed in U. S. Pat. Nos. 5,201,708, 5,242,240 and 5,318,538 are designed to allow the shields to be retracted from their locked, extended positions.

A shield system for protecting the piercing element of a prefilled syringe is also disclosed in European Publication No. EP 0 740 942 A1. The disclosed system includes a holder which is coupled to the flange of the syringe barrel, and a shield which is telescopically mounted to the holder. Two hands are required to operate this system.

SUMMARY OF THE INVENTION

This invention relates to a safety shield system for a syringe, medical cartridge or the like and such a system as used in combination with an assembly capable of functioning as a syringe. In accordance with the preferred embodiment of the system, the user is able to cause the shielding of a needle cannula by simply applying additional pressure to the plunger rod of the syringe following injection of the contents of the syringe barrel. The shield may accordingly be deployed automatically through the use of only one hand. As there is no need to place the hand near the needle for any purpose, the risk of needle stick injury is further reduced.

In accordance with the objects of the invention, a medical device is provided which includes an automatically operable shield system mounted to a syringe barrel. The system includes a tubular holder which defines an enclosure. A tubular needle shield is slidably attached to the holder and preferably telescopically received within the holder. The syringe barrel is received within the holder and shield assembly, preferably within the tubular shield, and the shield is extendable from a retracted position, wherein the needle cannula is exposed to an extended position, wherein the shield encloses the needle cannula following injection. A compressed spring is located within the holder and shield assembly which biases the shield axially toward the extended position. The shield is releaseably retained to the holder, such that upon application of force to the stopper following injection, the shield is released from the retracted position and the spring drives the shield to the extended position. In the disclosed embodiment, the shield includes a stop member adjacent its proximal end and the holder includes a stop member adjacent its distal end which releaseably retains the shield in its retracted position. In the preferred embodiment, the stop member on the holder is an annular internal groove adjacent the distal end of the holder and the stop member on the shield is a radially outwardly extending annular rib. In the most preferred embodiment, the shield includes a further stop member in the form of a second radial rib adjacent the proximal end of the shield which engages the stop member on the holder when the shield is extended to its extended position. The force of the compressed spring by itself is insufficient to disengage the stop member adjacent the distal end of the shield and the stop member on the holder. However, axial movement of the syringe following injection, disengages the stop members and releases the shield. It is intended to cover the needle tip when in the extended position. The syringe barrel is operably coupled to the shield such that sufficient axial movement of the syringe barrel causes axial displacement of the shield sufficient to cause disengagement of the stop members. Such movement of the barrel is ordinarily caused by pressure on the plunger rod of the syringe, driving the stopper against the end of the barrel following complete injection of the contents of the barrel. Upon disengagement of the first and second stop members, the spring causes the shield to move to the extended position.

The proximal end of the holder is preferably adapted to engage and retain the syringe flange upon receipt of the syringe barrel through the proximal end of the holder. The axial or distal movement of the shield is preferably limited by a second abutment surface or rib adjacent the proximal end of the shield which engages a radially inwardly projecting distal end portion of the holder. Such movement could alternatively be limited by a tether connecting the holder and shield. The shield is preferably positioned within the holder such that the spring engages a stop member extending radially outwardly from the shield. The opposite end of the spring can bear against any suitable surface, operably connected to the holder, preferably a flange on the end fitting.

The shield system according to the invention is comprised of a holder, a shield, a spring and an end fitting which receives the spring and which isolates the syringe from the holder, reducing damage to the syringe flange. The tubular shield is adapted for receiving a syringe. The shield is slidably mounted to the holder, and is movable between a retracted position, wherein the shield needle cannula is exposed and an extended position wherein the needle cannula is enclosed. A spring urges the shield towards the extended position. The holder includes a stop member which is engageable with a first stop member of the shield to maintain it in the retracted position. Sufficient axial movement of the syringe barrel causes disengagement of the stop members, allowing the spring to move the shield to the extended position. The holder is engageable with a second portion of the shield axially-spaced from the first portion to prevent decoupling of the shield and holder when the shield moves to the extended position. An end fitting is incorporated in the system to maintain the position of the spring prior to insertion of a syringe into the holder, prevent direct contact of the spring and the syringe flange and isolate the syringe flange from the holder during extension of the shield, preventing damage to the syringe flange.

The tubular holder includes an inwardly opening annular channel or chamber adjacent the open proximal end which receives the flanges of the syringe and fitting. The chamber includes opposed first and second abutment surfaces to retain the flanges. The fitting is located within the holder and includes a tubular portion surrounding the proximal end of the shield and a flange portion located within the housing chamber between the flange of the syringe barrel and the first abutment surface spaced distally from the proximal abutment surface. In the disclosed embodiment, the flange portion of the fitting includes a radially outwardly extending portion and a radially inwardly extending portion. In the preferred embodiment, the radially outwardly extending portion includes at least one and preferably a plurality of resiliently deformable projections extending toward the first abutment surface which isolates the flange of the barrel from the housing and damps impact of the syringe barrel against the first abutment surface, significantly reducing the likelihood of damage such as cracking of the flange of a glass syringe barrel when the shield is extended to the extended position by the spring. In the most preferred embodiment, the resiliently deformable projections are diamond-shaped having a pointed end opposite the first abutment surface and the projections are integral with the fitting preferably formed of a resilient polymer. The radially inwardly projecting portion of the fitting flange portion receives the spring, which is preferably a coil spring biased between the radially inwardly projecting portion of the fitting and a radially outwardly extending rib on the shield which also serves as the second stop.

The shield system facilitates the safe use of prefilled syringes, although it can be adapted for other sharp-pointed injection devices, such as syringes filled just before use and other injection devices. When employed with a syringe, the system allows the contents of the syringe to be expressed in a conventional manner. Continued, and preferably increased pressure on the plunger rod following injection causes the syringe barrel to move axially, thereby axially displacing the shield. Such displacement causes release of the stop members, and the spring to move the shield over the needle of the syringe. Protection against needle sticks is accordingly provided.

DETAILED DESCRIPTION OF THE INVENTION

An injection device 10 for injecting a medicament, drug or vaccine into a patient is shown in FIGS. 1–8. The device comprises a prefilled or prefillable syringe 12 and a shield assembly coupled to the syringe.

Figure 2:
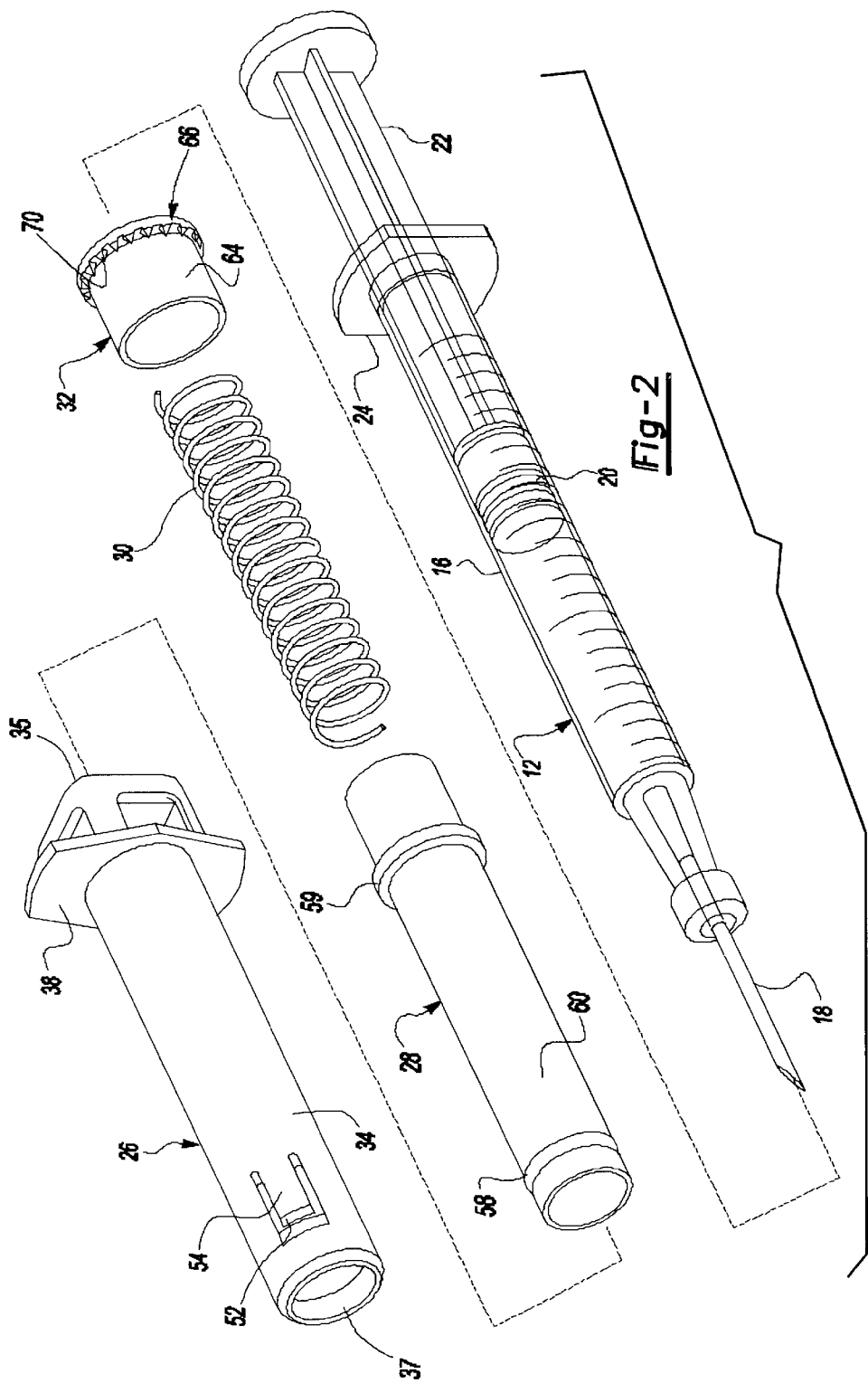
FIG. 2 is an exploded, perspective view thereof.

Syringes are ordinarily comprised of a tubular, generally cylindrical portion 16, known as a barrel, a needle cannula 18 or other piercing element or a connecting element secured to one end of the barrel, and a piston or stopper 20 slidably positioned within the barrel. The needle cannula may be removably secured to the barrel, but is more likely to be permanently secured to the barrel when the barrel is comprised of glass. Glass barrels are commonly used in prefillable syringes, and ordinarily contain a single dose of medication. Prefilled syringes made from plastic are also known to the art. Referring to FIG. 2, the shield system disclosed herein is employed in conjunction with a prefillable syringe 12 including a barrel 16, a cannula such as a needle 18 permanently secured to the barrel, a stopper 20 slidably positioned with the barrel, and a plunger rod 22 engageable with the stopper. The syringe barrel 16 includes a radially outwardly extending integral flange 24, which is normally grasped by the healthcare worker or patient but is used to couple the syringe to the shield system of this invention.

The shield system 14 according to this invention includes a tubular holder 26, a tubular shield 28 coupled to the holder, a coil spring 30 and an end fitting 32 which engages one end of the spring. With the exception of the spring 30 and the fitting 32, all of the components of the shield system may be made from a semi-rigid plastic material, such as polypropylene. The spring is preferably a metal coil spring. The fitting is preferably formed of a resilient polymer, such as a thermoplastic elastomer, rubber, synthetic rubber or a rubber blend.

The holder 26 is preferably comprised of an elongate, generally cylindrical tubular body 34 which defines a generally cylindrical enclosure. The holder has proximal and distal open ends 35 and 37, respectively, which provide access to the enclosure. A flange 38 extends radially outwardly from the holder body near the proximal open end 35 thereof. The flange and body of the holder are designed for easy handling as an injection is made. Only one hand should be required for injection.

Figure 1:
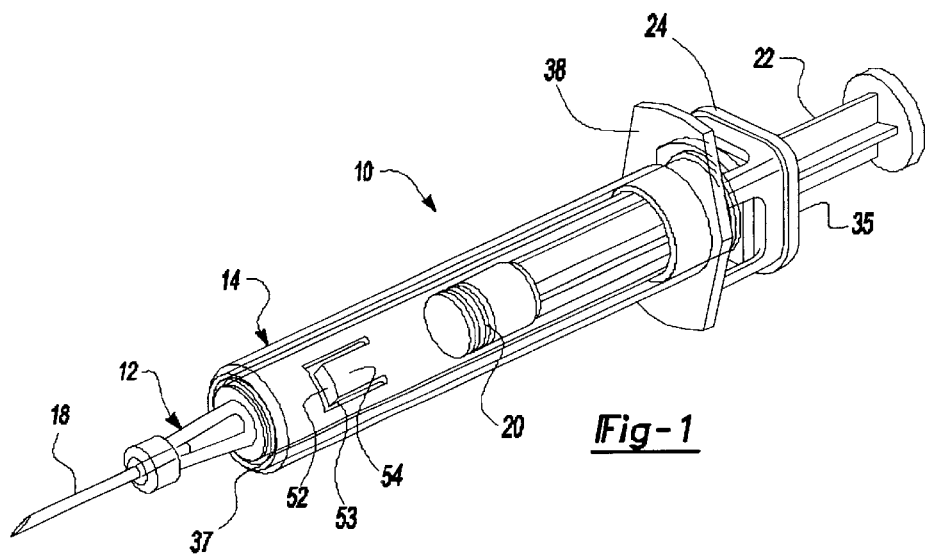
FIG. 1 is a top perspective view of a preferred embodiment of the medical device according to the invention as assembled.
Figure 3:
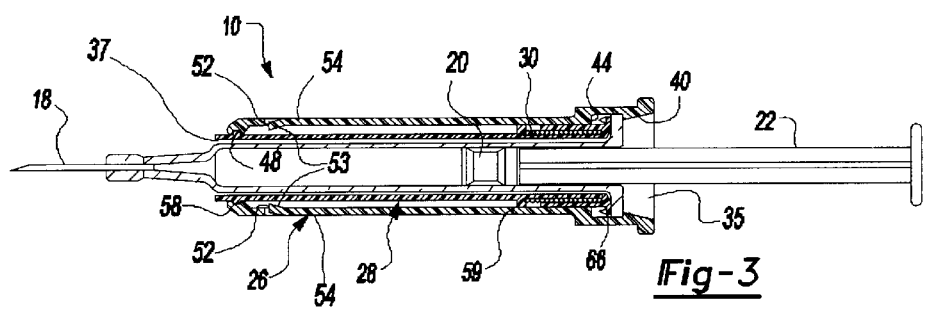
FIG. 3 is a sectional elevation view thereof.
Figure 4:
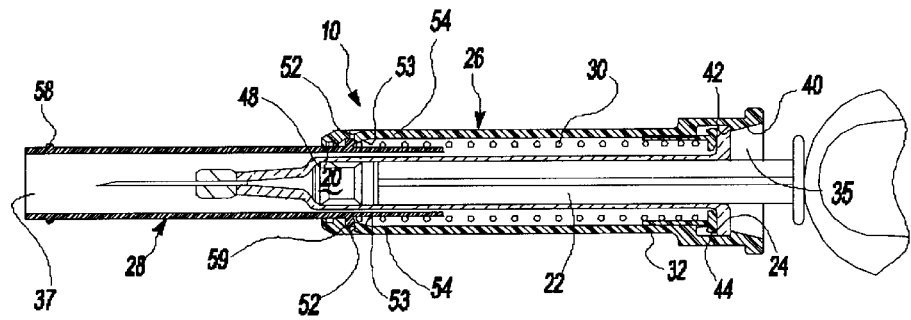
FIG. 4 is a sectional view thereof following actuation of the shield system of the device.
Figure 5:
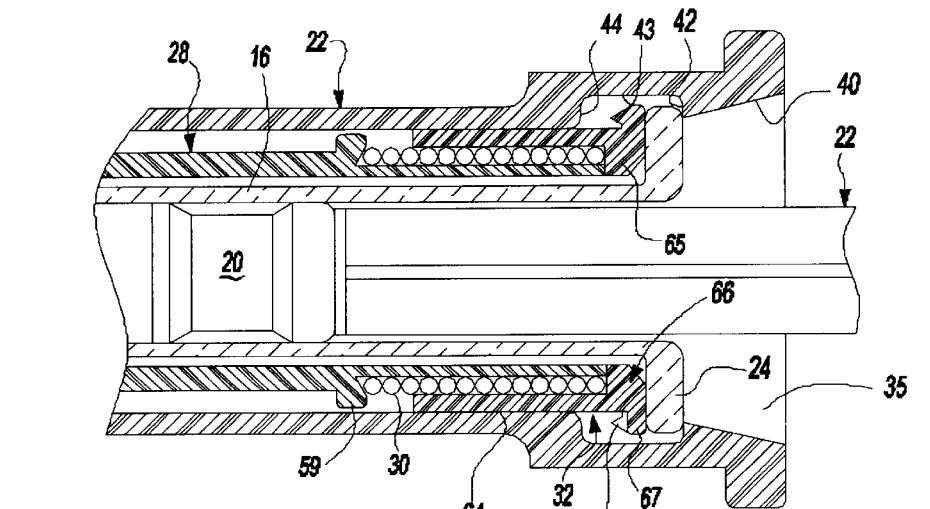
FIG. 5 is an enlarged sectional view of the proximal portion of the device prior to actuation of the shield system.
Figure 8:
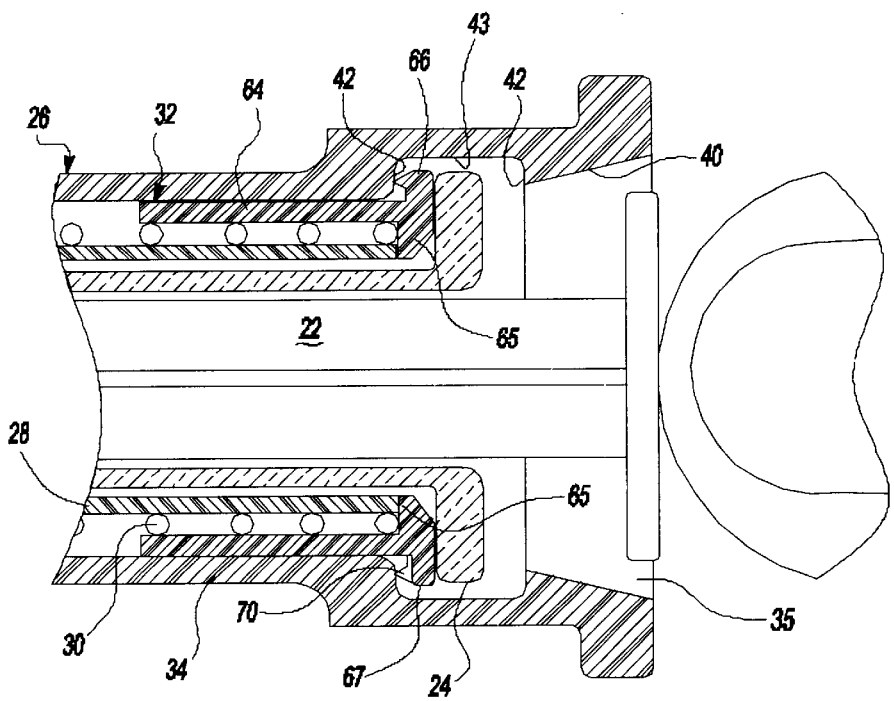
FIG. 8 is an enlarged sectional view of the proximal portion of the device immediately following actuation of the shield system.

The inner surface of the holder enclosure includes a frustoconical surface 40 adjoining the proximal open end 35 as shown in FIGS. 3 and 5. A first abutment surface 44 is formed by the holder body in opposing spaced relation to the second abutment surface 42. A second abutment surface 42 is formed at the inner end of this surface, as shown in FIGS. 4 and 5. As shown in FIGS. 5 and 8, the abutment surfaces 42 and 44 and the outer wall 43 form an annular channel or chamber for receipt of the syringe flange 24. The inner diameter of the holder, measured at the abutment surfaces 42 and 44, is smaller than the distance between the edges or major diameter of the syringe flange 24. Accordingly, once the syringe is inserted far enough into the holder such that the flange 24 is located between abutment surfaces 42, 44, it is slidably coupled to the holder. The frustoconical surface 40 facilitates this insertion. The spring 30 urges the syringe flange 24 towards engagement with the first abutment surface 42 as shown in FIG. 5. The gap formed between the abutment surfaces 42 and 44 is preferably greater than the thickness of the syringe flange 24 to allow large tolerances in height to ease clipping (particularly at high speed) and absorb flange thickness variations and system built up tolerances.

Figure 6:
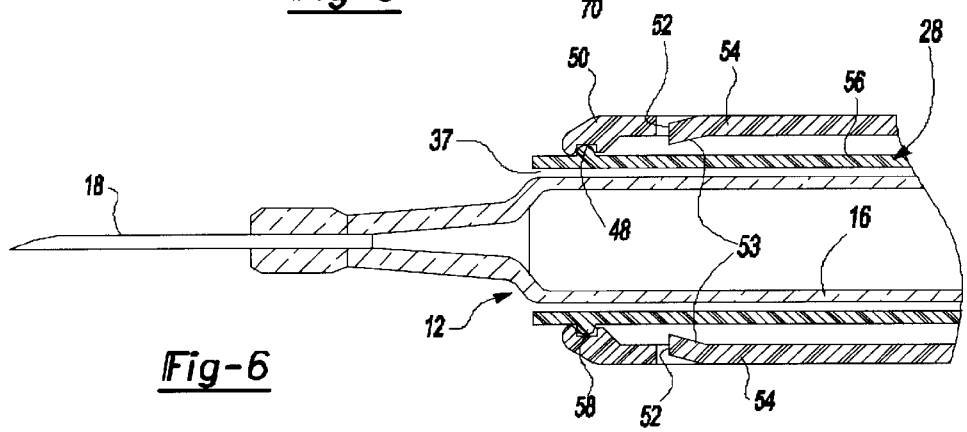
FIG. 6 is an enlarged sectional view showing a portion of the device, including the distal portion of a syringe holder of the device, prior to actuation of the shield system.
Figure 7:
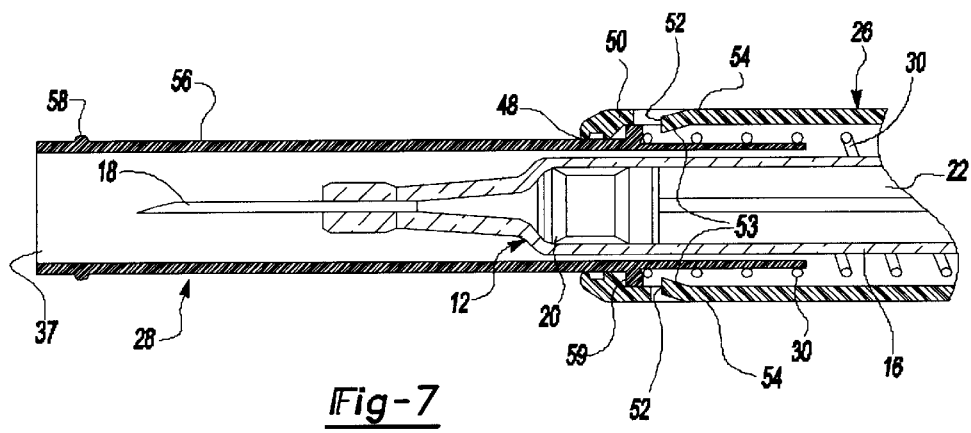
FIG. 7 is an enlarged sectional view showing a portion of the device including the distal portion of the syringe holder following actuation of the shield system.

A radial groove 48 or stop, best shown in FIGS. 6 and 7, is provided on the inside surface of the holder adjacent its distal end 37. The radial groove is provided in an arcuately inwardly projecting distal end portion 50 of the holder, which also serves as a stop member as described below.

A pair of opposed detents 52 are provided on the holder which prevent retraction of the shield 28 once extended. Each of these detents 52 is formed on an axially extending arm 54 which is integral with the holder body 34 and pivotable with respect thereto. (See FIGS. 2, 6 and 7.) The end surface of each detent 52 faces the distal open end 37 of the holder which is substantially perpendicular to the longitudinal axis of the holder. An inclined end surface 53 is provided on the opposite side of each detent, and faces the proximal open end 37.

The shield 28 is comprised of a substantially cylindrical tubular body 56. The tubular shield 28 preferably has an outside diameter small enough to be positioned within the holder and an inside diameter large enough to receive the barrel 16 of the syringe. As shown in FIGS. 2 and 7, a stop member 58 in the form of a radially outwardly extending collar or rib is formed integrally on the body 56 of the shield near the distal end thereof. A second, radially outwardly extending collar or rib 59 is formed integrally on the shield body 56 towards the proximal end, and defines another stop member 59. The second collar 59 is preferably larger in diameter than the first collar.

The coil spring 30 has an internal diameter large enough to fit over the proximal end of the shield, such that one end thereof bears against the collar 59. The opposite end of the spring bears against the radially inwardly projecting flange portion 65 of the flange portion or collar 66 of the end fitting 32 as shown in FIG. 5, and the flange portion 66 is biased against the flange 24 of the syringe barrel as shown in FIG. 5, such that the spring 30 is operably biased between the second abutment surface 42 of the holder 26 and the shield 28.

The spring 30 causes the shield 28 to move axially upon axial movement of the plunger rod 22 when the stopper 20 is driven against the proximal end of the barrel as shown in FIG. 4, with sufficient force to disengage the rib 58 on the shield from the groove 48 in the holder distal end as described further below. Direct engagement of the end fitting 32 or syringe flange 24 and shield, as provided in the preferred embodiment, is not necessary in such an arrangement. The operation of the device can be effected whether the shield, spring, end fitting and syringe barrel are directly or indirectly engaged, so long as axial movement of the syringe barrel causes axial movement of the shield.

The end fitting 32 includes a cylindrical tubular portion 64 which is inserted within the body 34 of the holder as shown in FIG. 8 and surrounds the proximal end of the shield 28 between the rib 59 and the proximal open end as shown in FIG. 5. As described above, the end fitting also includes a proximal flange portion 66 including a radially inwardly projecting portion 65 which receives the proximal end of the spring 30 and the flange portion 66 further includes a radially outwardly projecting flange portion 67 which extends into the annular channel or chamber defined by the opposed abutment surfaces 42 and 44 and the outer wall 43 as shown in FIGS. 5 and 8 and is located between the first abutment surface 44 and the flange 24 of the syringe barrel 16. The radially outwardly extending flange portion 66 has a diameter greater than the internal diameter of the opposed abutment surfaces 42 and 44 of the chamber adjacent the proximal open end 35 of the holder, such that the shield 28, spring 30 and fitting 32 are assembled and inserted through the open end 35 as shown in FIG. 5, wherein the radial outer flange portion 67 is biased against the frustoconical surface 40 as described above. The syringe barrel 16 is then inserted through the open end 35 or the shield assembly is assembled on the syringe barrel and inserted into the holder 22 as an assembly.

Prior to use, the spring 30 biases the flange portion 66 of the fitting 32 against the flange 24 of the syringe barrel 16, which biases the flange 24 against the second abutment surface 42 as shown in FIG. 5. The radially outwardly extending flange portion 67 is thus spaced from the first abutment surface 44 and the needle cannula 18 is exposed as shown in FIGS. 3 and 6 for injection. Following injection, the user further compresses the stopper 20 against the end of the syringe barrel 16, releasing or decoupling the stop members 48 and 58 and the spring 30 then drives the shield to its extended position as shown in FIG. 7. This sudden movement of the shield results in vibration of the syringe. Further, because the user is pressing against the distal end of the syringe barrel during release of the shield as shown in FIG. 8, the syringe flange cannot move to the right in FIG. 8. Thus, the flange 24 of the barrel may be driven against the radially outwardly extending portion 67 of the fitting against the first abutment surface 42. It has been found by the applicant that this vibration and sudden movement may result in damage including cracking of the flange 24 of the barrel 16 which, as set forth above, is generally formed of glass.

Figures 9, 10:
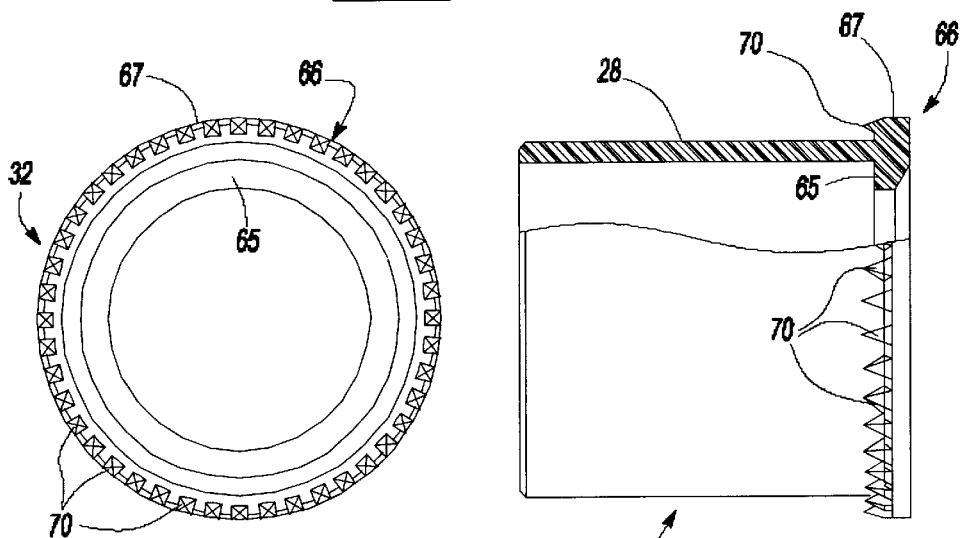
FIG. 9 is an end view of the end fitting.
FIG. 10 is a side, partially cross-sectioned view of the fitting shown in FIG. 9.

It would therefore be desirable to isolate the flange 24 of the syringe barrel from the holder 26 and damp impact of the syringe flange 24 and the radially outwardly projecting flange portion 67 against the abutment surface 42. This is accomplished in the present invention by providing resiliently deformable projections 70 which extend from the radially outwardly extending flange portion 67 of the fitting toward the first abutment surface 42 as best shown in FIGS. 5 and 8. These projections 70 isolate the flange 24 of the barrel 16 from the holder and prevent damage to the syringe flange 24. In the preferred embodiment, the flange portion 67 includes a plurality of spaced resiliently deformable projections 70. However, as will be understood, the object of the projections can also be fulfilled by a single continuous resiliently deformable projection. Further, in the preferred embodiment, the distal end of the resiliently deformable projection or projections 70 have a pointed distal end facing the abutment surface 42 providing improved damping by the projections. In the most preferred embodiment disclosed, the resiliently deformable projections are diamond-shaped as best shown in FIG. 9 providing excellent damping of vibration of the syringe flange 24 as shown in FIG. 8, wherein the shield 28 has just been released and the spring 30 is not yet fully expanded. As will be understood, the end fitting 32 also avoids direct contact of the coil spring against the fragile glass syringe flange 24. Further, in the most preferred embodiment, the resiliently deformable projection 70 are integral with the flange portion 66 and the tubular portion 28 for ease of manufacture and assembly. In such embodiments, the fitting 32 is preferably formed of a resilient polymeric material, such as a thermoplastic elastomer, rubber, synthetic rubber and blends. The improved end fitting 32 thus reduces damage to the flange 24 of the syringe barrel 16 and isolates the flange from the housing 22.

The assembly and use of this preferred embodiment of the invention will now be described. The shield 28 is slidably mounted to the holder 26 by inserting the shield through the proximal open end 35 thereof until the first stop member or collar 58 is received in the radial groove or stop member 48 in the holder. The spring is inserted through the proximal open end 35 of the holder, and over the shield until it abuts the relative large collar or rib 59. As a final step, prior to providing the shield system to the end user, the end fitting 32 is slipped over the exposed end of the spring and pushed through the proximal end 35 of the holder. The spring is substantially compressed during this step. The shield 28 is resiliently urged towards the distal end 37 of the holder 26 while the end fitting 32 is urged towards the proximal end thereof by the coil spring 30. Neither element can move due to the engagement of the stop members 48, 58, and the annular wall or collar 66 of the end fitting with the abutment surface 42, respectively. The force of the spring 30 is insufficient to cause the disengagement of the shield and holder.

The shield system 14 receives a syringe 12 of appropriate size through the proximal open end 35 of the holder. The system as shown is designed for receiving a syringe 12 including a flange 24. The syringe flange 24 engages the conical surface 40 and is inserted into the shield until the flange 24 snaps behind the first abutment surface 42 in the holder. The end fitting 32 is displaced axially slightly during this procedure. As the needle of the syringe is ordinarily protected by a needle cover or cap (not shown) at this time, it may be safely coupled to the shield system.

The force required to disengage the rib or stop 58 of the shield from the stop member or internal groove 48 of the holder is greater than the force of the spring plus the force required to expel the contents of the syringe barrel 16 by compressing the stopper 20. The plunger rod 22 is employed to move the stopper 20 through the syringe barrel until the contents of the barrel have been completely expelled. (The needle cover is, of course, removed prior to injection.) The contents of the barrel of a prefilled syringe ordinarily corresponds to a single dose of the prescribed medicament.

Following removal of the needle 18 from the patient, the user applies a greater force to the plunger rod 22 than that applied during injection. Such force causes axial displacement of the syringe barrel 16, end fitting 32, the spring 30 and the shield 28 with respect to the holder 28. The distance between the annular wall or collar 66 of the end fitting (or the flange 24) is then sufficient to permit the second stop member rib 58 to move far enough axially to where its retention by the groove 48 is overcome by the force of the spring. The first stop member 48 may also be displaced radially inwardly as such sliding occurs if sufficient flexibility of the holder body is provided.

Once the rib 58 and groove 48 are disengaged, the spring 30 expands rapidly, causing the shield 28 to slide axially or distally with respect to the holder 26 and syringe barrel. The collar 59 moves past the detents 54, causing them to deflect radially outwardly and then inwardly to their original positions. The collar 59 then engages the stop member 50 as shown in FIG. 7. The resiliently deformable projection or projections 70 on the fitting 32 damps vibration of syringe 12 during movement the shield 28 reducing damage to the flange 24. Upon such engagement, the needle cannula 18 is entirely and permanently enclosed and covered by the shield 28, as shown in FIGS. 4 and 7. The shield cannot be retracted sufficiently to expose the needle tip due to the engagement of the stop member or collar 59 with the detents 52. It cannot be removed from the holder as the collar 59 cannot move past the stop member 50.

The above-described procedure is particularly safe as it can be accomplished using only one hand. No second hand is required to move the shield, push a button or use any other actuating member to release the shield spring. The risk of accidental actuation of the shield through inadvertent contact with an actuating button is also eliminated. Moreover, a one-handed system is simpler for most people to use. It is readily apparent that the shield system can be adapted for use with syringes of various shapes and sizes without major modification.

The deployment of a shield in response to the axial displacement of a syringe barrel with respect to a holder is a safe and effective way of protecting against needle sticks. The preferred embodiment of the invention, as described above, provides advantages for the user as well as the manufacturer. The components are relatively easy to manufacture and assemble. It will be appreciated, however, that modifications can be made without changing the basic mode of operation of the device. For example, the stop member 58, of the shield, rather than being in the form of a collar, can simply be the end of the shield. The dimensions of each component of the medical device are determined by the specific uses(s) for which it is designed.

It will be appreciated and understood by those skilled in the art that further and additional revisions to the invention may be devised without departing from the spirit and scope of the appended claims, the invention not being limited to the specific embodiment shown.

What is claimed is:

1. An injection device, comprising:

a generally cylindrical tubular barrel including a first end having a needle cannula having a sharp distal end and a second open end having a radial flange adjacent said second open end;

a tubular holder surrounding said barrel including a first open end adjacent said first end of said barrel spaced from said sharp distal end of said needle cannula and a second open end having a chamber receiving said flange of said barrel, said chamber having an abutment surface facing said flange of said barrel;

a tubular shield releaseably retained by said holder located within said holder surrounding at least a portion of said barrel including a first open end and a second open end, said tubular shield axially moveable with respect to said barrel between a retracted position, wherein said sharp distal end of said needle cannula is exposed, to an extended position, wherein said sharp distal end of said needle cannula is enclosed by said shield;

a fitting within said tubular holder having a tubular portion surrounding said tubular shield and a radial flange portion located within said chamber of said tubular holder between said flange of said barrel and said abutment surface of said chamber having at least one resiliently deformable projection extending toward said abutment surface;

and a spring operably biased between said shield and said holder urging said shield from said retracted position toward said extended position when said shield is released from said tubular holder, whereby said resiliently deformable projection on said flange portion of said fitting damps movement of said flange of said barrel in said chamber, reducing damage to said flange of said barrel.

2. The injection device as defined in claim 1, wherein said resiliently deformable projection comprises a plurality of projections circumferentially spaced around said flange portion of said insert extending toward said abutment surface of said chamber.

3. The injection device as defined in claim 2, wherein said plurality of projections are integral with said flange portion of said fitting and said fitting is formed of a resilient polymer.

4. The injection device as defined in claim 2, wherein said plurality of projections are diamond-shaped each having a pointed distal end.

5. The injection device as defined in claim 1, wherein said tubular shield includes a radially outwardly extending rib and said spring is biased between said rib of said shield and said insert.

6. The injection device as defined in claim 5, wherein said insert includes an inwardly projecting radial portion and said spring is biased between said rib of said tubular shield and said radial portion of said insert.

7. The injection device as defined in claim 1, wherein said holder includes a first stop member adjacent said first open end and said tubular shield includes a first stop member adjacent said first open end of said tubular shield, wherein said first stop members of said holder and said shield releaseably retain said shield in said retracted position.

8. The injection device as defined in claim 7, wherein said tubular shield includes a second stop member axially spaced from said first stop member arresting movement of said tubular shield towards said extended position.

9. The injection device as defined in claim 8, wherein said tubular holder includes a second stop member adjacent to but spaced from said first stop member which prevents retraction of said shield from said extended position enclosing said needle cannula sharp distal end.

10. The injection device as defined in claim 1, wherein said injection device includes a stopper in said barrel telescopically moveable through said barrel to inject fluid through said needle cannula and a plunger attached to said stopper extending through said second open end of said barrel, whereby force applied to said stopper against a reduced diameter end portion of said barrel applies force to said barrel, releasing said tubular shield.

11. An injection device, comprising:
a generally cylindrical tubular barrel formed of glass including a first reduced diameter end portion having a needle cannula attached thereto having a sharp distal end and a second open end having an integral radial flange adjacent said second open end;
a stopper located in said barrel telescopically moveable through said barrel and a plunger attached to said stopper extending through said second open end of said barrel;

a tubular holder surrounding said barrel including a first open end adjacent said first open end of said barrel and a second open end having a chamber receiving said flange of said barrel, said chamber having an abutment surface facing said flange of said barrel;

a tubular shield located within said tubular holder surrounding at least a portion of said barrel releaseably retained by said holder including a first open end and a second open end, said tubular shield axially moveable with respect to said barrel between a retracted position, wherein said sharp distal end of said needle cannula is exposed, to an extended position, wherein said sharp distal end of said needle cannula is enclosed by said shield;

a fitting located within said tubular holder including a tubular portion surrounding said tubular shield and a radial flange portion located within said chamber of said holder between said flange of said tubular barrel and said abutment surface of said chamber, wherein said flange portion of said fitting includes at least one resiliently deformable projection extending toward said abutment surface of said chamber; and a coil spring surrounding said tubular shield adjacent said second end resiliently biased between said shield and said flange portion of said fitting urging said shield from said retracted position toward said extending position when said shield is released, whereby said resiliently deformable projection on said flange portion of said fitting damps movement of said flange of said barrel in said chamber, reducing damage to said flange of said barrel.

12. The injection device as defined in claim 11, wherein said chamber in said holder includes a second abutment surface having a diameter less than an outside diameter of said flange of said barrel, retaining said flange in said chamber.

13. The injection device as defined in claim 12, wherein said second open end of said tubular holder includes an inwardly tapered surface permitting assembly of said flange of said barrel in said chamber.

14. The injection device as defined in claim 11, wherein said tubular shield includes a radially outwardly projecting rib spaced from said second open end of said shield and said coil spring is biased between said radially outwardly projecting rib of said shield and said flange portion of said fitting.

15. The injection device as defined in claim 11, wherein said tubular holder includes a stop member adjacent said first open end and said tubular shield includes a complimentary stop member adjacent said first open end and said stop members releaseably retaining said shield in said retracted position.

16. The injection device as defined in claim 11, wherein said at least one resiliently deformable projection comprises a plurality of projections circumferentially spaced around said flange portion of said insert.

17. The injection device as defined in claim 16, wherein said plurality of spaced projections are integral with said flange portion of said fitting and said fitting is formed of a resilient polymer.

18. The injection device as defined in claim 16, wherein said plurality of projections are diamond-shaped each having a pointed distal end.

19. An injection device, comprising:
a generally cylindrical tubular barrel including a reduced diameter first open end having a needle cannula secured thereto having a sharp distal end and a second open end having a radial flange adjacent said second open end;

a tubular holder surrounding said barrel including a first open end adjacent said first open end of said barrel and a second open end having a chamber therein receiving said flange of said barrel, said chamber having opposed first and second abutment surfaces, wherein said first abutment surface faces said flange of said barrel;

a tubular shield located within said tubular holder surrounding at least a portion of said barrel releaseably retained by said holder including a first open end and a second open end, said tubular shield axially moveable with respect to said barrel between a retracted position, wherein said needle cannula is exposed, to an extended position, wherein said needle cannula is enclosed by said shield;

a fitting within said tubular holder having a flange portion located within said chamber of said tubular holder between said flange of said barrel and said first abutment surface including a plurality of resiliently deformable projections circumferentially spaced around said flange portion; and a spring resiliently biased between said shield and said insert biasing said flange of said barrel against said second abutment surface of said chamber when said shield is in said retracted position, whereby said resilient projections damp movement of said flange of said barrel in said chamber, reducing damage to said flange, when said shield is extended to said extended position.

20. The injection device as defined in claim 19, wherein said plurality of projections are integral with said flange portion of said fitting and said fitting is formed of a resilient polymer.

21. The injection device as defined in claim 19, wherein said plurality of projections on said flange portion of said fitting are diamond-shaped each having a pointed distal end.

22. The injection device as defined in claim 19, wherein said chamber include a gap formed between opposed first and second abutment surfaces has a dimension greater than the thickness of the flange of said barrel.

* * * * *